(12) United States Patent
Isgar

(10) Patent No.: US 11,350,863 B2
(45) Date of Patent: Jun. 7, 2022

(54) WORRY STONE DEVICE AND SYSTEM

(71) Applicant: Charles Isgar, Scottsdale, AZ (US)

(72) Inventor: Charles Isgar, Scottsdale, AZ (US)

(*) Notice: Subject to any disclaimer, the term of this patent is extended or adjusted under 35 U.S.C. 154(b) by 0 days.

(21) Appl. No.: 17/201,935

(22) Filed: Mar. 15, 2021

(65) Prior Publication Data
US 2022/0104745 A1    Apr. 7, 2022

Related U.S. Application Data

(60) Provisional application No. 63/086,232, filed on Oct. 1, 2020.

(51) Int. Cl.
*A61B 5/16*    (2006.01)
*A61B 5/00*    (2006.01)

(52) U.S. Cl.
CPC .............. *A61B 5/165* (2013.01); *A61B 5/742* (2013.01)

(58) Field of Classification Search
CPC ................................ A61B 5/165; A61B 5/742
See application file for complete search history.

(56) References Cited

U.S. PATENT DOCUMENTS

| | | | | |
|---|---|---|---|---|
| 2014/0139466 A1* | 5/2014 | Sakaguchi | ............ | G06F 1/1694 345/173 |
| 2015/0073285 A1* | 3/2015 | Albert | ............ | H04B 5/0043 600/509 |
| 2017/0027509 A1* | 2/2017 | Martinez | ............ | A61B 5/02055 |
| 2017/0333666 A1* | 11/2017 | Goldberg | ............ | A61B 5/6801 |
| 2018/0033330 A1* | 2/2018 | Darmour | ............ | G06Q 10/10 |
| 2018/0116607 A1* | 5/2018 | Yu | ............ | A61B 5/681 |
| 2018/0300008 A1* | 10/2018 | Rasanen | ............ | G06F 3/04883 |
| 2019/0307983 A1* | 10/2019 | Goldman | ............ | A61M 21/02 |
| 2019/0336724 A1* | 11/2019 | Li | ............ | A61B 5/742 |
| 2020/0005663 A1* | 1/2020 | Welles | ............ | G06K 9/00302 |
| 2020/0090813 A1* | 3/2020 | Hann | ............ | A61B 5/744 |

OTHER PUBLICATIONS

"MyWorryStone—Apps on Google Play." Google, Google, play.google.com/store/apps/details?id=com.tekniika.android.myworrystone. Updated Nov. 17, 2018 (Year: 2018).*

\* cited by examiner

*Primary Examiner* — Mallika D Fairchild
*Assistant Examiner* — Nathan A Baldwin
(74) *Attorney, Agent, or Firm* — Schmeiser, Olsen & Watts LLP

(57) ABSTRACT

A worry stone system is provided. The system includes a worry stone device having an internal sensing and processing system, a user computing device, and a server having a memory storing worry stone data. The server may be programmed to receive worry stone data from the worry stone device through the user computing device in near real-time that includes contact time between the user and the worry stone device, a rate of rubbing the worry stone device, and/or a pressure used for rubbing the worry stone device. The server may process the worry stone data and send the same for display on the user computing device. The server operates to continuously process received near real-time worry stone data and send the processed worry stone data for display on the user computing device during the entire time of engagement of the worry stone device by the user.

16 Claims, 12 Drawing Sheets

WORRY STONE DEVICE AND SYSTEM

CROSS REFERENCE TO RELATED APPLICATION

This application claims priority to U.S. Provisional Patent Application to Charles Isgar entitled "WORRY STONE DEVICE AND SYSTEM," Ser. No. 63/086,232, filed Oct. 1, 2020, the disclosure of which is hereby incorporated entirely herein by reference.

BACKGROUND OF THE INVENTION

Technical Field

This invention relates generally to a worry stone, and more particularly to an electronic worry stone device that is connectable to a user computing device for receiving and capturing data corresponding to rubbing of the worry stone device.

State of the Art

Worry stones are typically rocks, gemstones or the like and are usually in the shape of an oval or something similar easy to hold in the hand. Worry stones often have, but not required to have, a thumb-sized indentation, and are generally used for relaxation or anxiety relief. They are typically used by holding the worry stone between the index finger and thumb and gently moving one's thumb back and forth across the stone to rub the worry stone. This action of moving one's thumb back and forth across the stone can reduce stress. The drawback of worry stones is that the effect of use of the worry stone is not quantifiable and is left purely to identification by the user of the worry stone. Additionally, there is no tracking of how a person engages with the worry stone, the frequency of engagement, and so forth that may be meaningful in identifying stressors of the user and the use of the worry stone in coping with those stressors to keep anxiety at bay. There lacks a historical database of information that can be used by the user to predict or even avoid stressful situations. Such as device and system does not exist.

Accordingly, there is a need for a worry stone device and system that can track data related to engagement with the worry stone device.

DISCLOSURE OF THE INVENTION

The present invention relates to an electric worry stone device and system, wherein the worry stone device includes an internal sensing and processing system to sense the users engagement with the worry stone device, wherein the internal sensing and processing system can be coupled to a user computing device for communicating information sensed and processed by the worry stone device to the user computing device.

An embodiment includes a worry stone system comprising: a worry stone device having an internal sensing and processing system; a user computing device coupled to the worry stone device; and a server having a memory storing worry stone data, wherein the user computing device is coupled to the server through a connection established by an app operating on the user computing device, and wherein the server is programmed to: receive a signal from the user computing device that the worry stone device is engaged by a user in response to the worry stone device communicating engagement by the user to the user computing device and the user computing device accessing the system; automatically process the signal and identify the user and any of the stored worry stone data associated with the user; receive a signal comprising near real-time worry stone data, wherein the near real-time worry stone data comprises contact time between the user and the worry stone device, a rate of rubbing the worry stone device, and/or a pressure used for rubbing the worry stone device; automatically process the signal and store the worry stone data and send to the user computing device for display on a screen of the user computing device a user interface showing the near real-time worry stone data; and continuously receive the signal comprising near real-time worry stone data, processing the signal and sending the near real-time worry stone data for display on the user computing device during the engagement of the worry stone device by the user.

The user may rub the worry stone device for relaxation. The user may rub the worry stone device for stress relief. The user may rub the worry stone device for passing time. The user may rub the worry stone device for reducing screen time. More than one worry stone device may be used. A wearable device may be coupled to the user computing device. The worry stone device may be virtual and displayed on the screen of the user computing device. The worry stone device may be a key fob. The worry stone device may be coupled to a case of the user computing device. The worry stone device may be manufactured as part of the case. The worry stone device may be coupled to the case by adhesive. The worry stone device may be coupled to a gear shift of a vehicle. The worry stone device may be textured. The texture of the worry stone device may be smooth. The texture of the worry stone device may be rough.

The foregoing and other features and advantages of the present invention will be apparent from the following more detailed description of the particular embodiments of the invention, as illustrated in the accompanying drawings.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF EMBODIMENTS OF THE INVENTION

As discussed above, embodiments of the present invention relate to an electronic worry stone device and system, wherein the worry stone device includes an internal sensing and processing system to sense the users engagement with the worry stone device, wherein the internal sensing and processing system can be coupled to a user computing device for communicating information sensed and processed by the worry stone device to the user computing device. The system may include the use of a mobile application or even a web app operating on a user computing device that may be a mobile computing device like a smartphone, a tablet, a wearable, and the like. The system may also include the use of programmed instructions operating on a server and communicating with the user computing device in order to provide functionality of the system. Embodiments may be utilized for various benefits, such as, relaxing, stress relief, passing time, reducing screen time, collectively engaging in worry stone efforts in a social network manner and the like.

Figure 1:
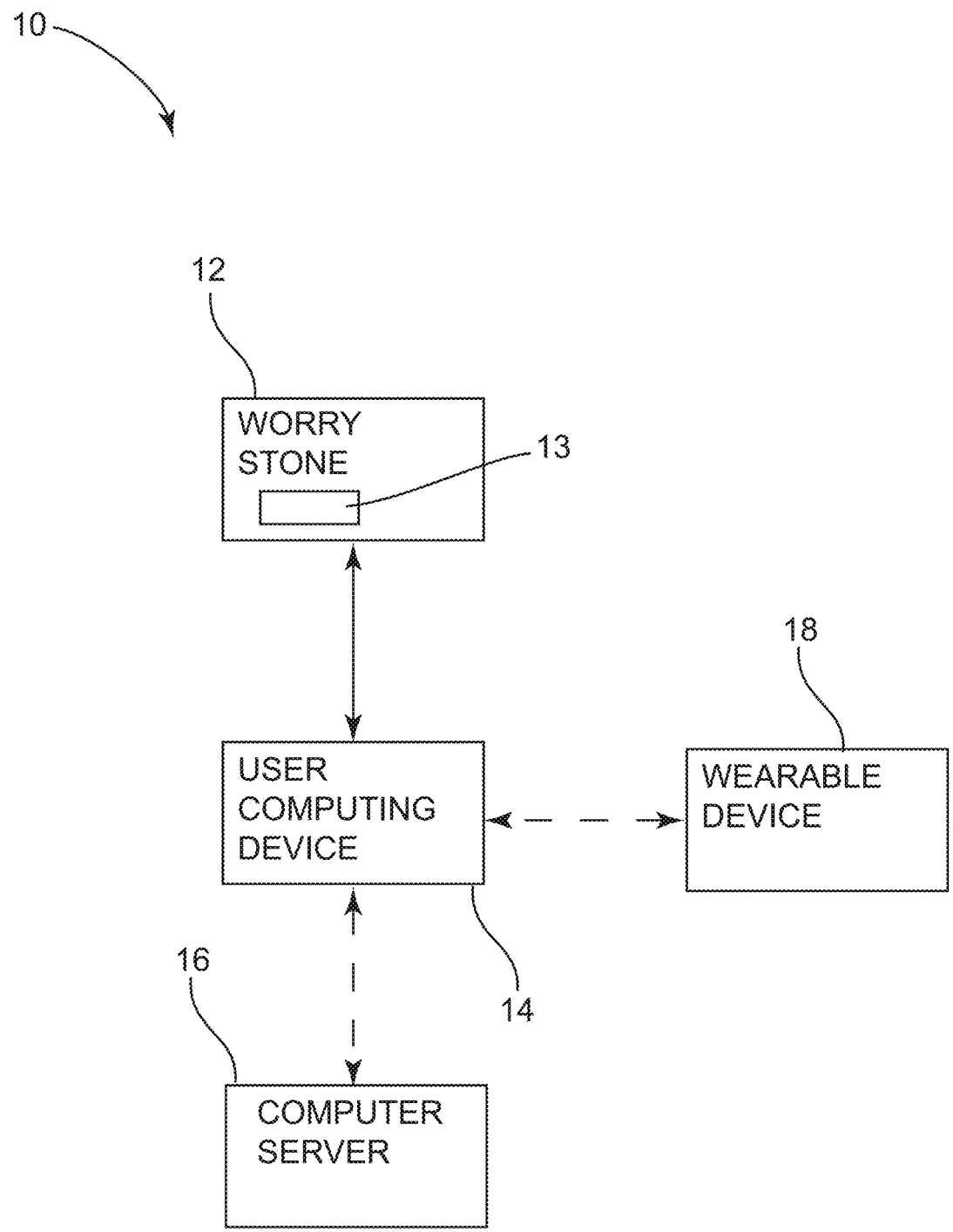
FIG. 1 a diagrammatic view of a worry stone system according to an embodiment.

Referring to the drawings, FIG. 1 depicts an embodiment of a worry stone system 10 that includes an electronic worry stone device 12, a user computing device 14, and a computer server 16. The worry stone device 12 may be a small portable device that includes a sensing and processing system 13. The sensing and processing system 13 may include one or more sensors for sensing rubbing of the worry stone device 12, contact time between the user and the worry stone device 12, a rate or frequency of rubbing the worry stone device 12, a pressure used for rubbing the worry stone device, and/or the like. The sensing and processing system may include internal memory and a processor, wherein the internal memory includes programming to process the data received from the sensors in real-time or near real-time, save temporarily in memory and process the data for sending to the user computing device 14. The sensing and processing system 13 may also include communication hardware and protocols to couple the sensing and processing system to the user computing device 14. The coupling between the worry stone device 12 and the user computing device 14 and the wearable device 18 may be a wireless connection, such as, but not limited to a Bluetooth connection, a Wi-Fi connection or the like for transmission of communication between the worry stone device 12 and the user computing device 14 and the wearable device 18 and the user computing device 14. The user computing device 14 may also be coupled to the computer server 16. The coupling between the user computing device 14 and the server 16 may be a network connection, such as through an Internet connection, wherein the user computing device 14 may communicate with and receive communication from the server 16. The user computing device 14 may include a laptop, a tablet, a smartphone, wearable devices and the like. The server 16, in some embodiments, may be a computer server or a cloud-based infrastructure architecture.

The server 16 may include a memory storing worry stone data including user identification and sensed data associated with the user regarding the user's engagement with the worry stone device 12, such as, but not limited to, the user's rubbing of the worry stone device 12, pressure applied during rubbing, the frequency or rate of rubbing the worry stone device, and the like. The worry stone data may be stored and aggregated over time to show a history of the user and the engagement of the worry stone.

Figure 2:
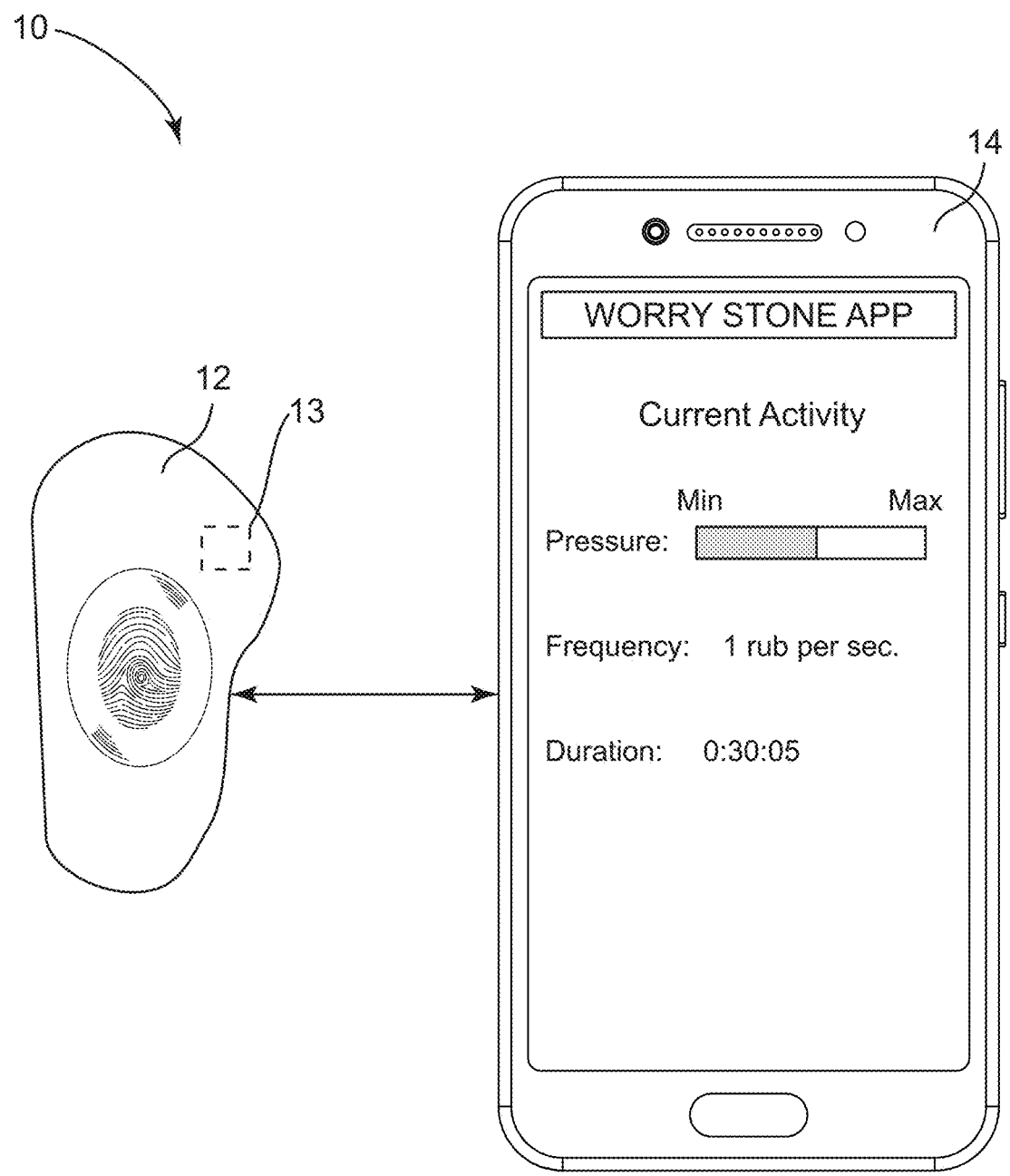
FIG. 2 is a front view of a worry stone device and a user computing device operating worry stone app of a worry stone system in accordance with an embodiment.

The system 10 may include use where the user rubs the worry stone to engage the worry stone for a purpose, such as, but not limited to, reducing stress, in memory or support of another and so forth. In accordance with this embodiment, the worry stone device 12 may be coupled to the user computing device 14, and the user computing device 14 may be coupled to the server 16. Referring to FIG. 2, the server 16 (not shown) may be programmed receive a signal from the user computing device 14 that the worry stone device 12 is engaged by a user in response to the worry stone device 12 communicating engagement by the user to the user computing device 14 and the user computing device 14 accessing the system 10; automatically process the signal and identify the user and any stored worry stone data associated with the user; receive a signal comprising near real-time worry stone data, wherein the near real-time worry stone data comprises a rate of rubbing the worry stone device 12, a pressure used for rubbing the worry stone device 12, and a total time of worry stone device 12 engagement by the user; automatically process the signal and store the worry stone data and send to the user computing device 14 for display on a screen of the user computing device 14 a user interface showing the near real-time worry stone data; and continuously receive the signal comprising near real-time worry stone data, processing the signal and sending the near real-time worry stone data for display on the user computing device 14 during the entire time of engagement of the worry stone device 12 by the user. As shown in FIG. 2, worry stone data, such as, but not limited to, frequency of rubbing the worry stone device 12, pressure used during rubbing and total time of engagement with the worry stone device 12 may be depicted.

Figure 3:
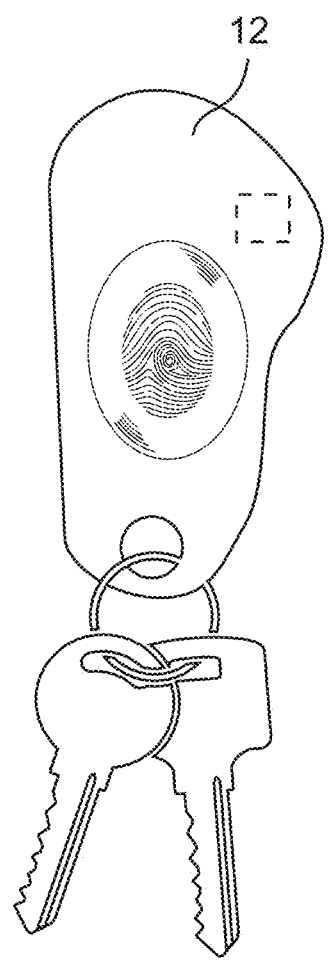
FIG. 3 is a front view of a worry stone device that is a key fob in accordance with an embodiment.
Figure 4:
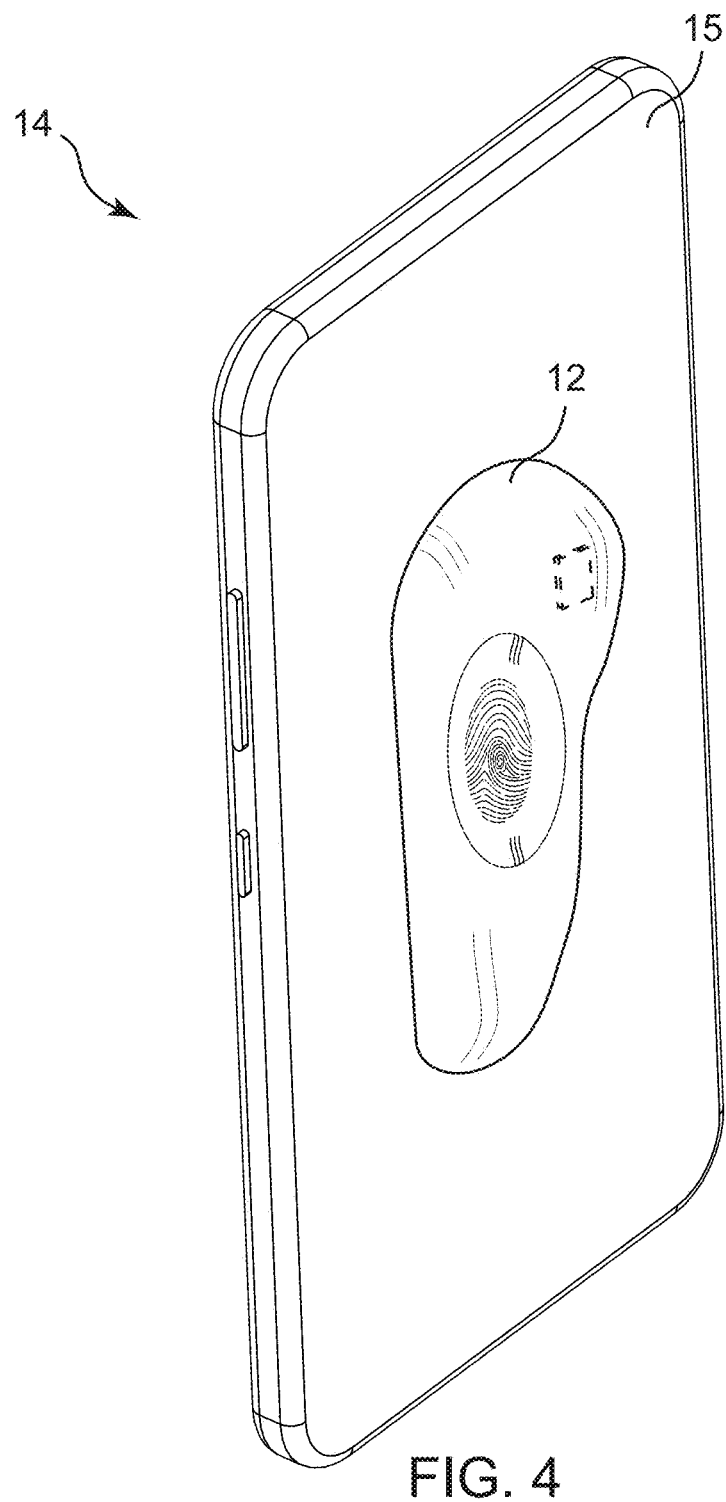
FIG. 4 is a front view of a worry stone device that is formed in a smartphone case in accordance with an embodiment.
Figure 6:
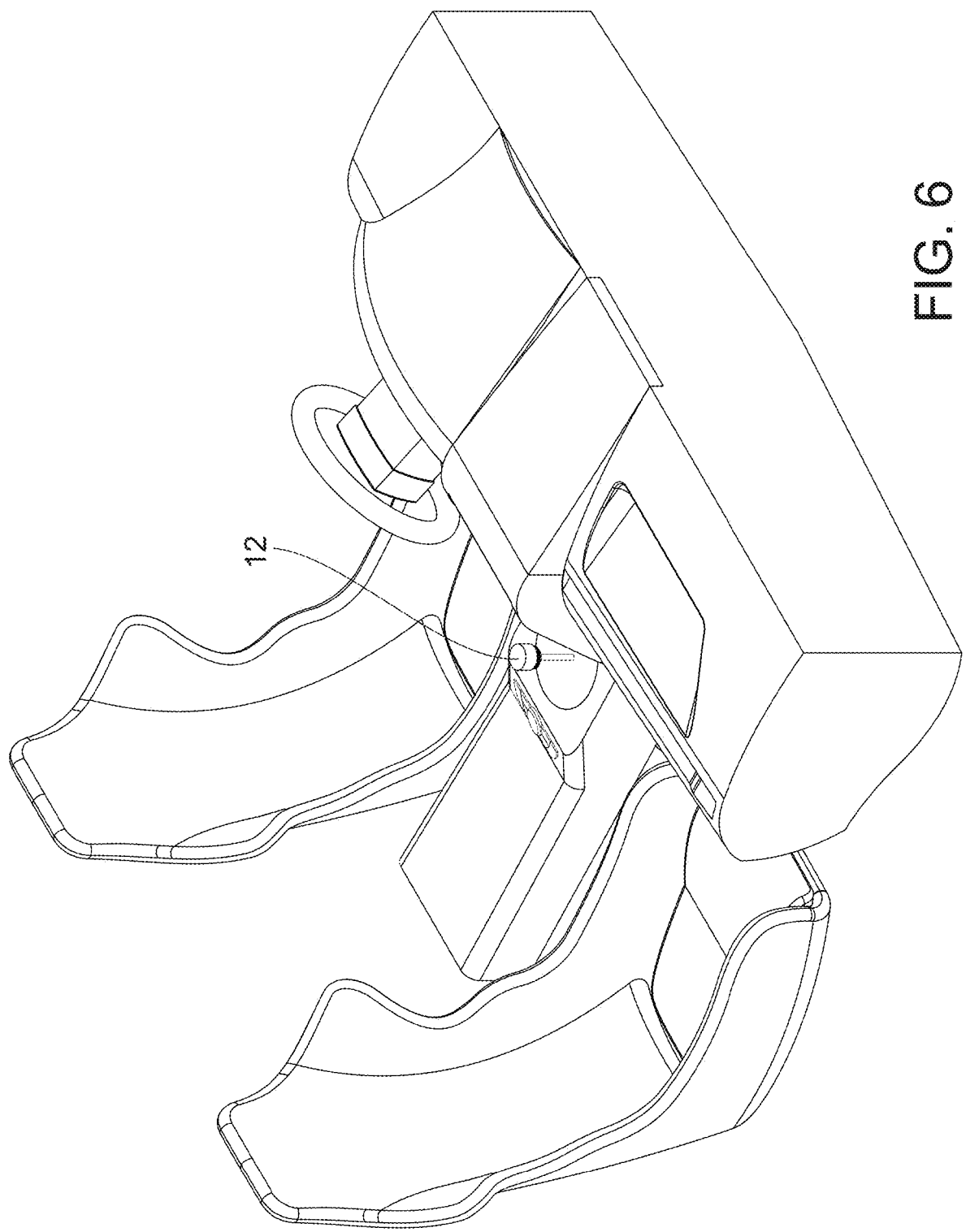
FIG. 6 is a front view of a worry stone device that is cover of a gear shift of a vehicle in accordance with an embodiment.
Figure 7:
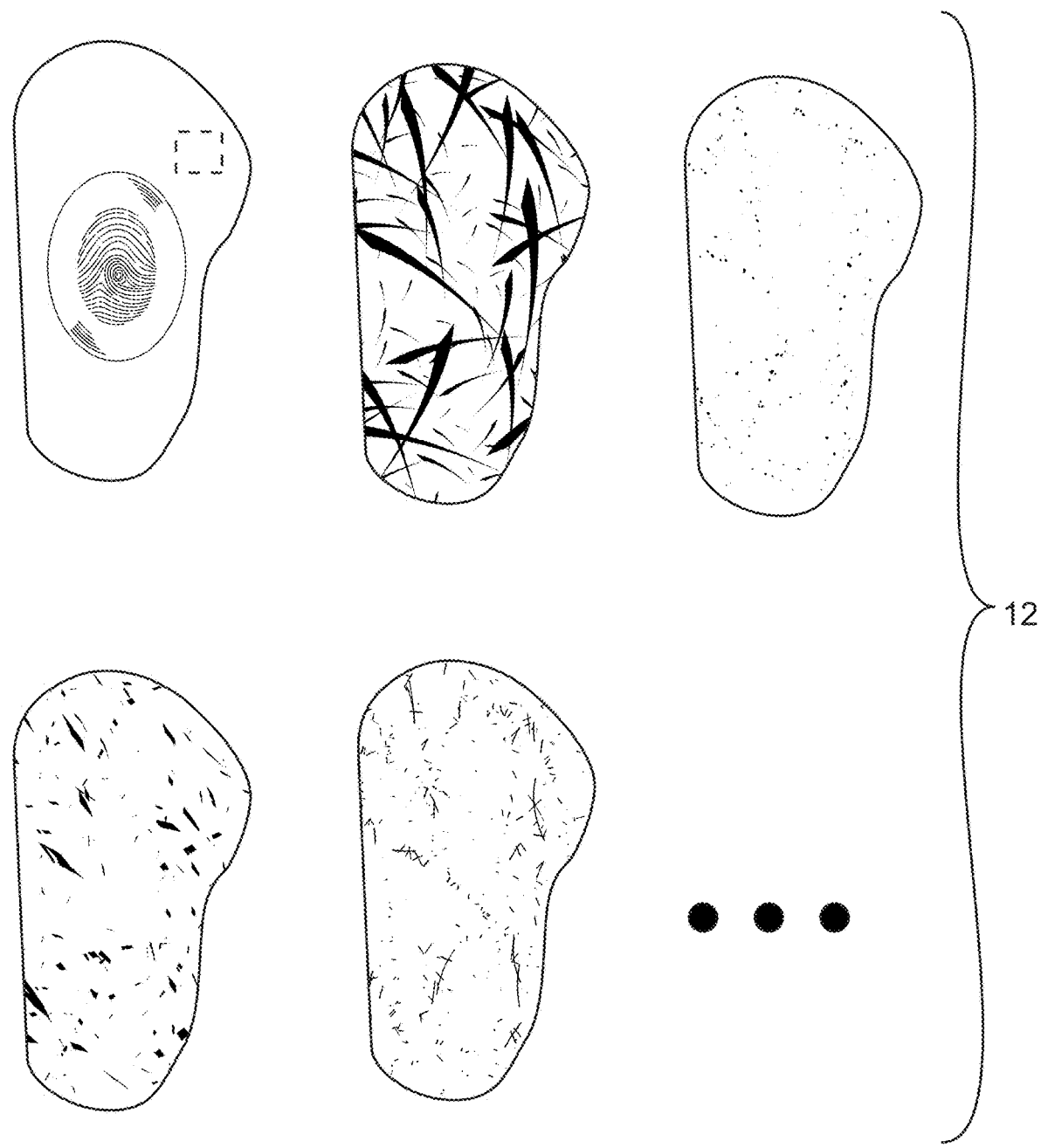
FIG. 7 is a front view of various textures of worry stone devices in accordance with an embodiment.

The worry stone device 12 may come in various forms and each may be utilized by any user within the worry stone system 10. For example, the worry stone may be a key fob, as shown in FIG. 3, allowing the user to continually have the worry stone in his or her pocket or purse while carrying keys. Another example is a worry stone device 12 coupled to a case 15 of a user computing device 14, as shown in FIG. 4. This may be a smartphone 14 and the stone may be coupled to the case 15, such manufactured as part of the case 15, coupled to it by adhesive or other form of coupling and so forth. Another example, as shown in FIG. 6, is a worry stone device 12 coupled to a gear shift of a vehicle, wherein the worry sone device 12 is available to rub during driving, such as in stressful driving conditions like rush hour or the like. It will be understood that these are just examples of various forms of a worry stone device 12 and should not be considered a limitation. Further, various textures of a worry stone device is contemplated, as depicted in FIG. 7, wherein the worry stone device 12 may be any type of texture or level of smoothness/roughness as represented by the various textures in FIG. 7.

Figure 5:
FIG. 5 is a front view of a worry stone device that is a virtual worry stone on the user computing device in accordance with an embodiment.

Further still, the worry stone device 12 may be a virtual worry stone device 12 as shown in FIG. 5, wherein the user can have the stone displayed on a screen of the user computing device 14 and rub the screen in order to rub the virtual stone. It will be understood that in these embodiments, the native sensors of the user computing device 14 may be utilized to operate in the manner that the sensing and processing system 13 does within a physical worry stone device 12. The user computing device 14 sensors may operate to sense and produce worry stone data that includes rubbing of the worry stone device 12, contact time between the user and the worry stone device 12, a rate or frequency of rubbing the worry stone device 12, a pressure used for rubbing the worry stone device, and/or the like. The system 10 may operate in the same manner as if using a physical worry stone device 12.

Figure 8:
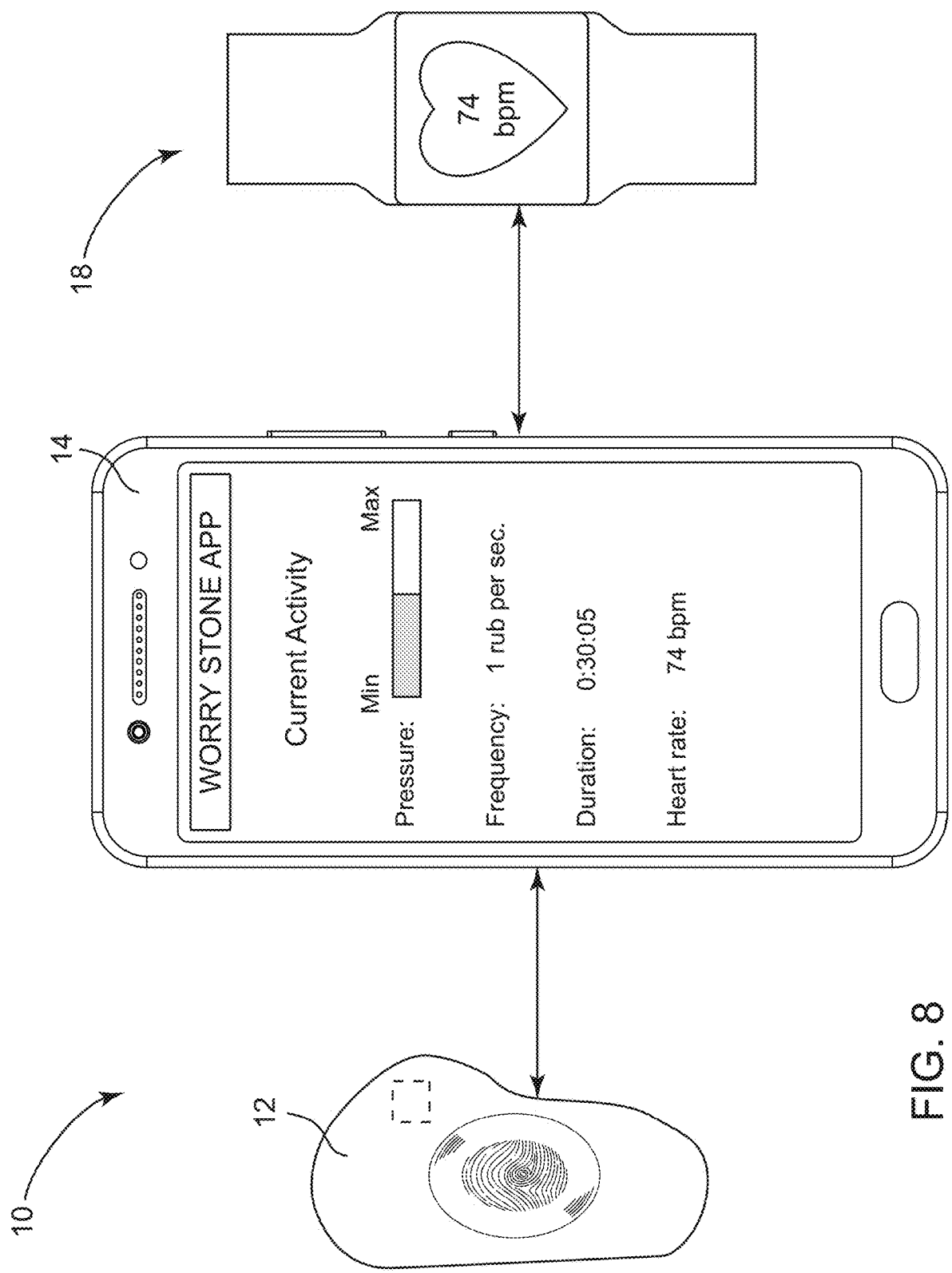
FIG. 8 is a front view of a worry stone device, a user computing device operating worry stone app of a worry stone system and a wearable device coupled to the user computing device in accordance with an embodiment.
Figure 9:
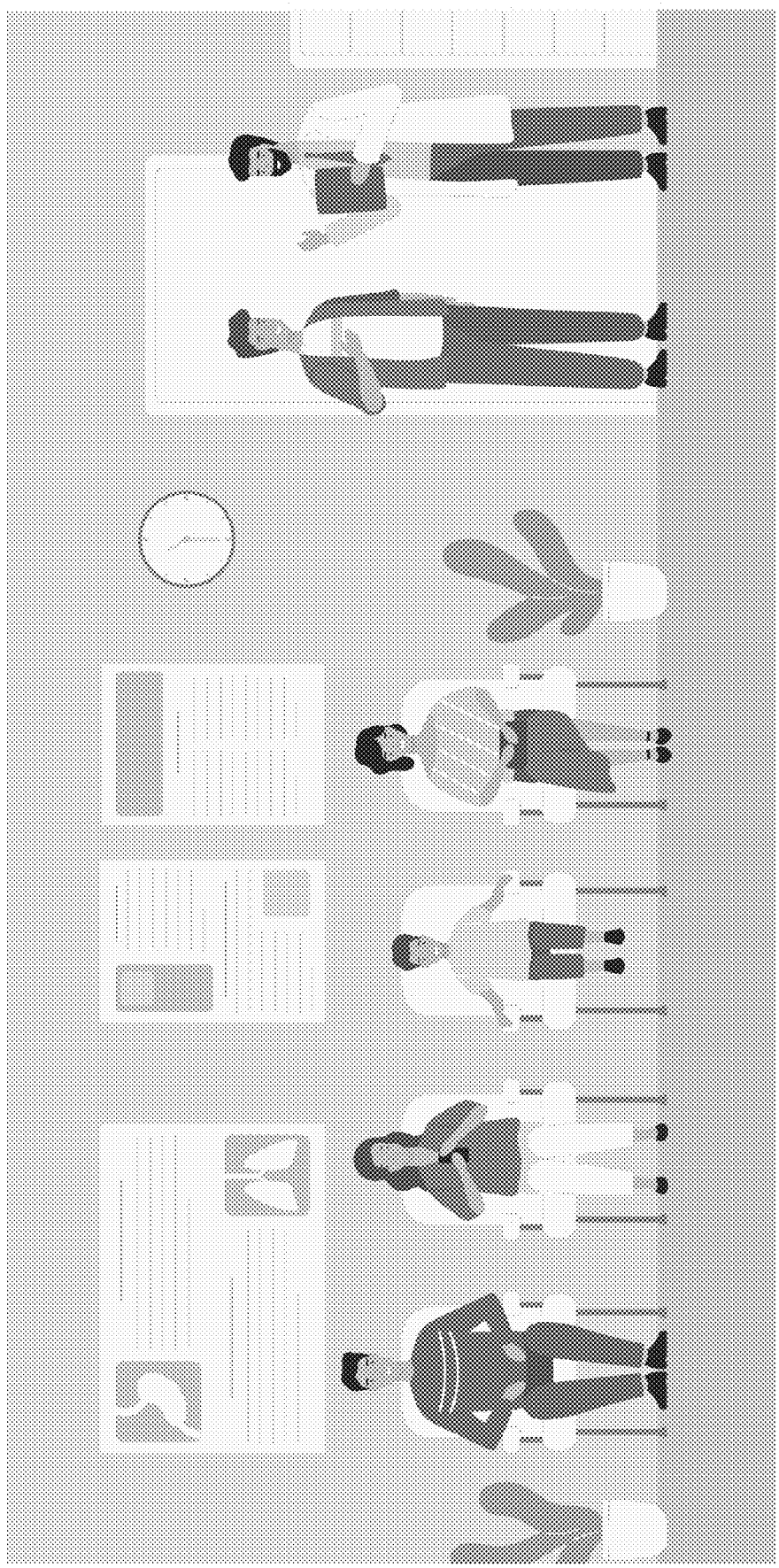
FIG. 9 is a view of a medical waiting room for use of a worry stone system in accordance with an embodiment.

Referring to the drawings again, FIG. 8 depicts the worry stone system 10 that may also include a wearable device 18 coupled to the user computing device 14. The wearable device 18 may provide additional user biometric data, such as, but not limited to, heart rate, blood oxygen level, electrocardiogram results, sleep data and the like. Some or all of this biometric data may be stored by the system 10 as worry stone data. The biometric data from the wearable device 18 may be aggregated with the sensed data from the worry stone device 12 and may be utilized by system 10 to identify correlations between rubbing of the worry stone device 12 and the effect that has on the biometric data collected from the wearable device 18. An example is depicted in FIG. 8, wherein the wearable device 18 is sending a biometric data of heartrate to the user computing device 14. This is collected in addition to the worry stone data, such as frequency of rubbing the stone, pressure used for rubbing and total time of rubbing the worry stone device 12. A stressful situation experienced by a user, such as, but not limited to, waiting in a waiting room to see a doctor, as shown in FIG. 9, often results in the user's body releasing adrenaline, that temporarily causes the user's breathing and heart rate to speed up and the user's blood pressure to rise. The user can then monitor his or her heart rate and the effect of the rubbing the worry stone device 12 has on the heart rate, which may be an indicator of the stress the user's body is feeling due to the stressful situation. The user may then have a historical record of the frequency, pressure and duration of rubbing the worry stone device 12 to deal with the stressful situations. This also allow the system 10 to utilize machine learning, wherein in some embodiments, the server may be programmed to analyze the historical aggregate worry stone data and biometric data stored in memory of the server 16 and predict and suggest a frequency, pressure and duration of rubbing the worry stone device 12 by the user in order to deal with the stress based on the heart rate and/or other biometric data collected. This suggested engagement of the worry stone device 12 may be sent from the server for display on the user computing device 14. In embodiments, the server 16 may alert the user computing device 14 when the biometric data is at a level of low or normal stress. Such a system may require the collection of biometric data from the wearable device 18 at times of no or little stress in order to set a baseline or reference value for each of the biometric data collected.

Figure 12:
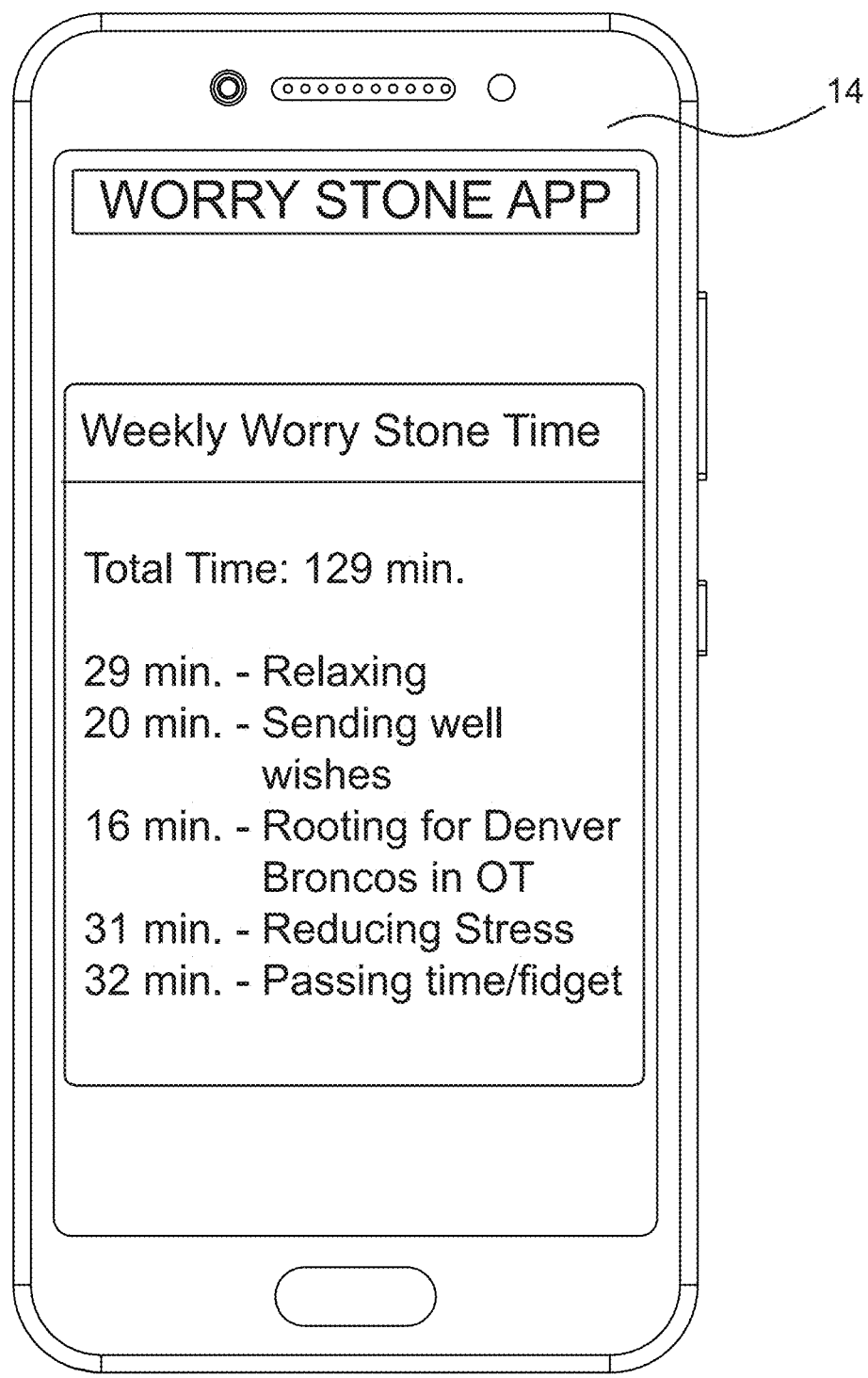
FIG. 12 is a view of a user computing device of a worry stone system showing weekly engagements of a worry stone by the user in accordance with an embodiment.

The system 10 may include an opportunity for the user to review his or her use of the worry stone device 12. FIG. 12 depicts a user computing device 14 depicting a weekly summary of the user's contact with the worry stone device 12. For example, the user may have spent a total of 129 minutes contacting his worry stone device 12. That total time may be depicted along with a breakdown of the total time, such as, but not limited to 29 minutes relaxing, 20 minutes sending well wishes to a friend in surgery, 16 minutes rooting for the Denver Broncos during overtime, 31 minutes reducing stress and 32 minutes passing time or fidgeting. It will be appreciated that the user ribbing his worry stone device 12 results in a reduced use of the user computing device 14, thereby reducing the screen time of the user, providing a dual benefit of relaxing or reducing stress and reducing screen time.

Figure 10:
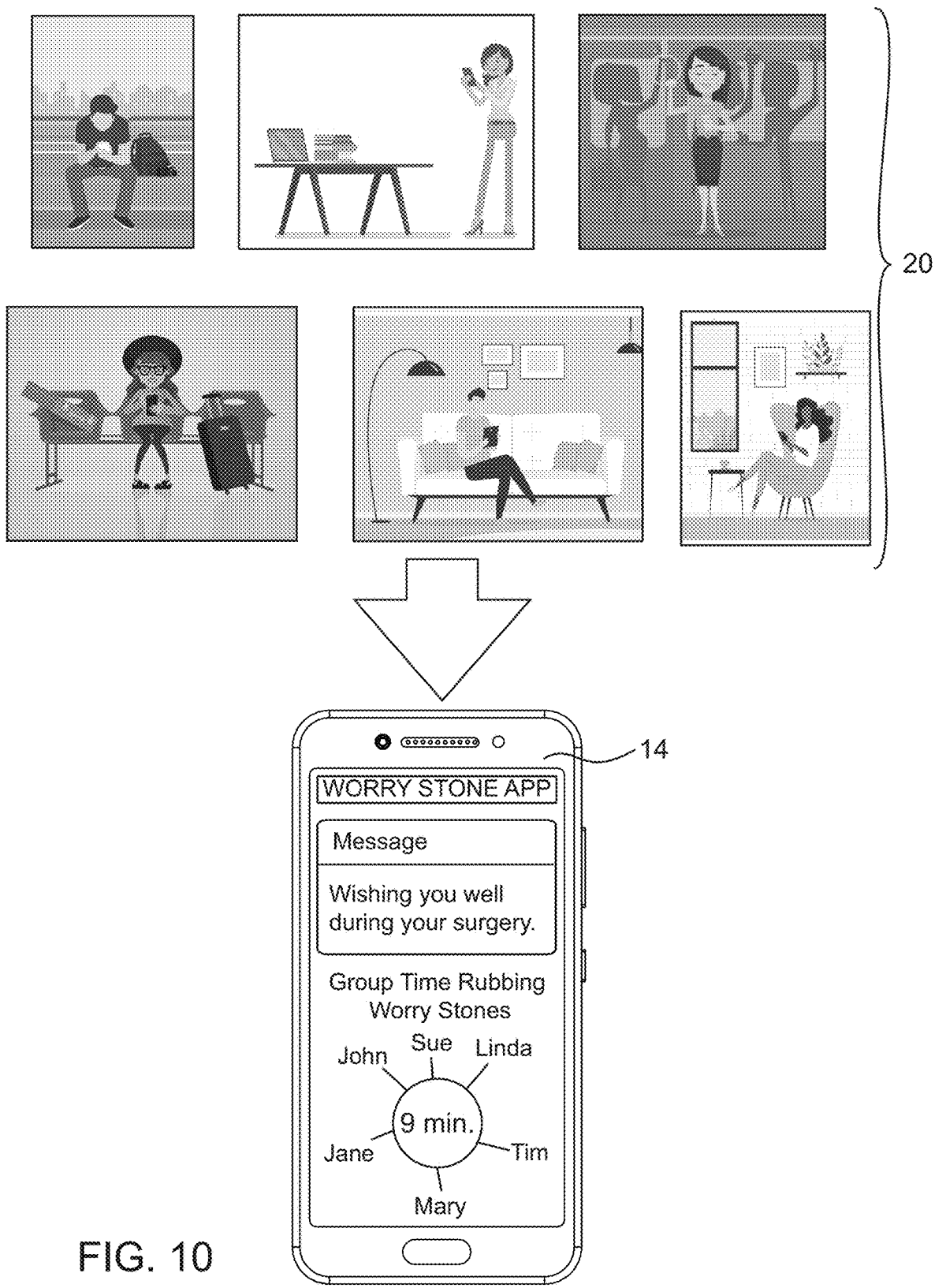
FIG. 10 is a view of a social network utilization of a worry stone system in accordance with an embodiment.
Figure 11:
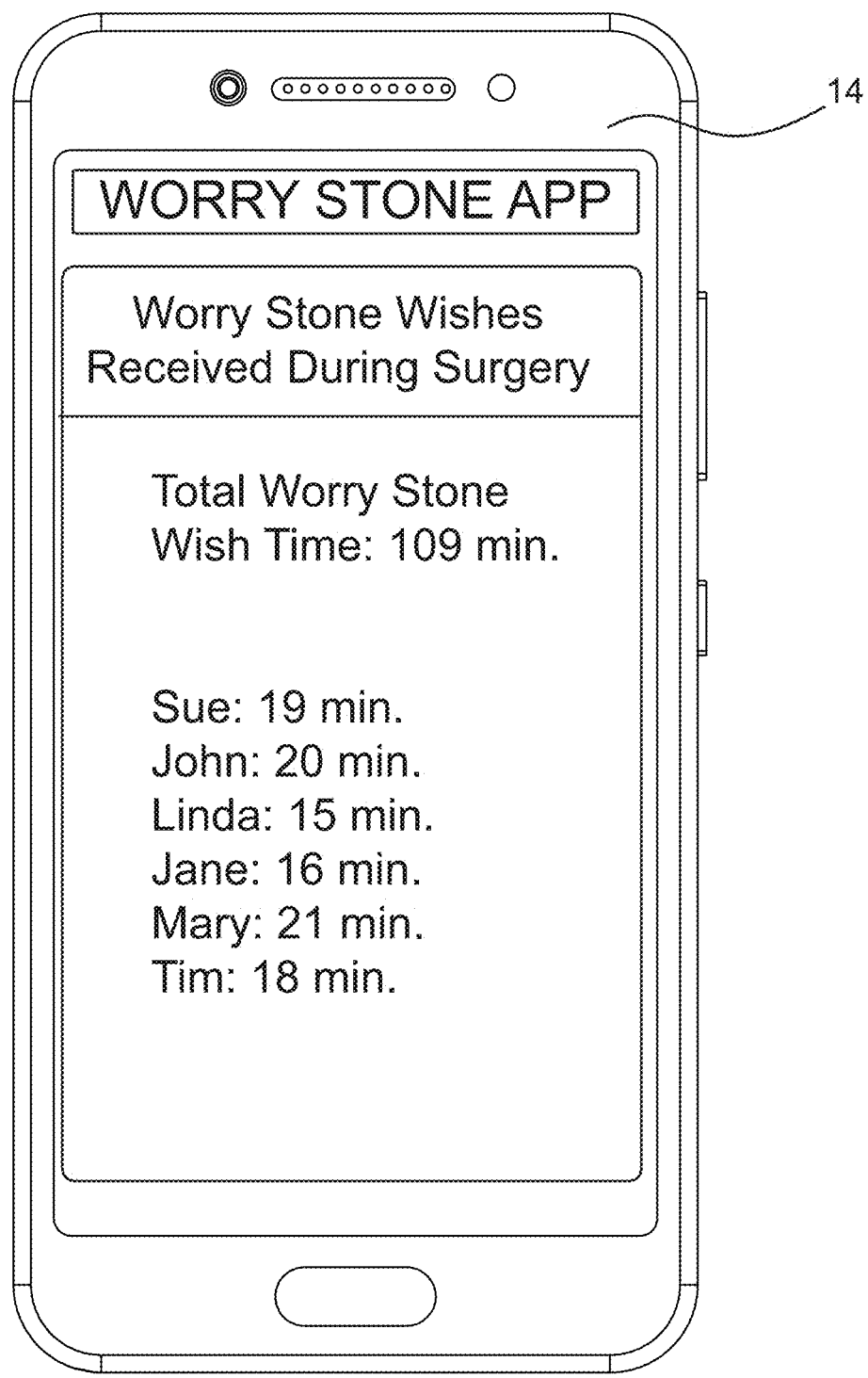
FIG. 11 is a view of a user computing device of a worry stone system showing received worry wishes from a group of friends as depicted in FIG. 10 in accordance with an embodiment.

Referring to FIG. 10, there is a social networking aspect to a worry stone system 10. As shown in FIG. 10, a group of individuals such as friend group 20 may engage with each socially on the worry stone app. FIG. 10 depicts one such social engagement wherein one of the members of the friend group 20 that is associated with the user computing device 14 depicted in the drawing is undergoing surgery. The friend group 20 may engage in a group worry stone session in an effort to send well wishes to the friend undergoing surgery. The server 16 may be programmed to send a message from the friend group 20 to the user computing device 14 having surgery and depict the names and time of those engaged in the group worry session. Further, referring to FIG. 11, the server 16 may be programmed to send for display on the user computing device 14 a time that the friend group 20 were engaged in the worry stone session sending well wishes, wherein it can display a total time of a group worry stone session, and may display the time each individual of the group has rubbed his or her own worry stone. This is just an example of one way of utilizing the system 10 in a social network capacity.

While it has been shown and described that the system includes a server 16, it will be understood that the user computing device 14 may operate without connection to a server 16, wherein the user computing device 14 is programmed to perform the same function as the server 16 and have a memory that stores the same data (worry stone data and biometric data) as the server 16 stores. The system would then be the worry stone device 12 and mobile computing device 14 with an optional wearable device 18.

Embodiments may be available on or through the internet, such as through domain names reserved and owned by Applicant that include worryfob.com, worryrub.com, worryphone.com, phone-stone.com, stone2phone.com, worrycircle.com or the like.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, cloud-based infrastructure architecture, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A worry stone system comprising:
   a worry stone device having an internal sensing and processing system for sensing worry stone data, wherein the worry stone device is a physical device;
   a wearable device having sensors for sensing biometric data;
   a user computing device coupled to the worry stone device and the wearable device; and
   a server having a memory storing the worry stone data and the biometric data, wherein the user computing device is coupled to the server through a connection established by an app operating on the user computing device, and wherein the server is programmed to:
      receive a signal from the user computing device that the worry stone device is engaged by a user in response to the worry stone device communicating engagement by the user to the user computing device and the user computing device accessing the worry stone system;
      automatically process the signal and identify the user and any of the stored worry stone data associated with the user;
      receive a signal comprising near real-time worry stone data and the biometric data, wherein the near real-time worry stone data comprises contact time between the user and the worry stone device, a rate of rubbing the worry stone device, and a pressure used for rubbing the worry stone device;

automatically process the signal and store the worry stone data and send to the user computing device for display on a screen of the user computing device a user interface showing the near real-time worry stone data; and continuously receive the signal comprising the near real-time worry stone data, processing the signal and sending the near real-time worry stone data for display on the user computing device during the engagement of the worry stone device by the user, wherein the server is programmed to analyze the stored worry stone data and biometric data in the memory of the server and predict and suggest the duration of rubbing, the rate of rubbing, and the pressure used for rubbing the worry stone device by the user.

2. The worry stone system of claim 1, wherein the user rubs the worry stone device for relaxation.

3. The worry stone system of claim 1, wherein the user rubs the worry stone device for stress relief.

4. The worry stone system of claim 1, wherein the user rubs the worry stone device for passing time.

5. The worry stone system of claim 1, wherein the user rubs the worry stone device for reducing screen time.

6. The worry stone system of claim 1, further comprising more than one worry stone device.

7. The worry stone system of claim 1, wherein, the worry stone device is a key fob.

8. The worry stone system of claim 1, wherein the worry stone device is coupled to a case of the user computing device.

9. The worry stone system of claim 8, wherein the worry stone device is manufactured as part of the case.

10. The worry stone system of claim 8, wherein the worry stone device is coupled to the case by adhesive.

11. The worry stone system of claim 1, wherein the worry stone device is coupled to a gear shift of a vehicle.

12. The worry stone system of claim 1, wherein the worry stone device is textured.

13. The worry stone system of claim 12, wherein the texture of the worry stone device is smooth.

14. The worry stone system of claim 12, wherein the texture of the worry stone device is rough.

15. The worry stone system of claim 1, wherein the suggestion is sent from the server for display on the user computing device.

16. The worry stone system of claim 1, wherein the server alerts the user computing device when the biometric data is at a predetermined level of stress.

* * * * *